United States Patent
Yun

(10) Patent No.: US 8,491,459 B2
(45) Date of Patent: *Jul. 23, 2013

(54) EXPANDABLE VESSEL HARNESS FOR TREATING VESSEL ANEURYSMS

(75) Inventor: Anthony Joonkyoo Yun, Palo Alto, CA (US)

(73) Assignee: Palo Alto Investors, Palo Alto, CA (US)

(*) Notice: Subject to any disclaimer, the term of this patent is extended or adjusted under 35 U.S.C. 154(b) by 338 days.

This patent is subject to a terminal disclaimer.

(21) Appl. No.: 12/759,544

(22) Filed: Apr. 13, 2010

(65) Prior Publication Data

US 2010/0262220 A1 Oct. 14, 2010

Related U.S. Application Data

(63) Continuation of application No. 11/318,336, filed on Dec. 23, 2005, now Pat. No. 7,722,529.

(60) Provisional application No. 60/639,481, filed on Dec. 28, 2004.

(51) Int. Cl.
*A61F 2/06* (2006.01)

(52) U.S. Cl.
USPC .......................................................... 600/37

(58) Field of Classification Search
USPC .............. 600/37, 16; 606/157, 237; 623/1.11, 623/1.15; 607/129
See application file for complete search history.

(56) References Cited

U.S. PATENT DOCUMENTS

| | | | |
|---|---|---|---|
| 5,366,504 A | 11/1994 | Andersen et al. |
| 5,562,726 A | 10/1996 | Chuter |
| 5,713,948 A | 2/1998 | Uflacker |
| 5,758,420 A | 6/1998 | Schmidt et al. |
| 6,063,104 A | 5/2000 | Villar et al. |
| 6,152,956 A | 11/2000 | Pierce |
| 6,287,335 B1 | 9/2001 | Drasler et al. |
| 6,506,204 B2 | 1/2003 | Mazzocchi |
| 6,585,748 B1 | 7/2003 | Jeffree |
| 6,592,605 B2 | 7/2003 | Lenker et al. |
| 6,599,302 B2 | 7/2003 | Houser et al. |
| 6,605,101 B1 | 8/2003 | Schaefer et al. |
| 6,682,557 B1 | 1/2004 | Quiachon et al. |
| 6,746,468 B1 | 6/2004 | Sepetka et al. |
| 6,814,748 B1 | 11/2004 | Baker et al. |
| 6,893,392 B2 | 5/2005 | Alferness |
| 6,929,654 B2 | 8/2005 | Teoh et al. |

(Continued)

OTHER PUBLICATIONS

Creech et al. "Traumatic Arteriovenous Fistula at Unusual Sites," Annals of Surgery (1965) 161 (6):908-920.

(Continued)

*Primary Examiner* — Christine Matthews
(74) *Attorney, Agent, or Firm* — Bret E. Field; Louis-Vu T. Nguyen; Bozicevic, Field & Francis LLP

(57) ABSTRACT

A harness for treating vessel aneurysms is disclosed. The harness applies elastic, compressive reinforcement on the aneurysm to reduce deleterious wall tension and to resist the shape change of the vessel. Rather than imposing a dimension beyond which the aneurysm cannot expand, the harness provides no hard limit over the range of systolic expansion of the vessel. Instead, the harness follows the contour of the vessel throughout systole and continuously exerts gentle resistance to stretch. Also disclosed is a method of delivering the vessel harness to the vessel with minimal invasion.

5 Claims, 2 Drawing Sheets

U.S. PATENT DOCUMENTS

| | | | |
|---|---|---|---|
| 6,949,113 | B2 | 9/2005 | Van Tassel et al. |
| 6,969,401 | B1 | 11/2005 | Marotta et al. |
| 7,025,779 | B2 | 4/2006 | Elliott |
| 7,722,529 | B2* | 5/2010 | Yun .............................. 600/37 |
| 2002/0028981 | A1* | 3/2002 | Lau et al. ..................... 600/37 |
| 2003/0033005 | A1 | 2/2003 | Houser et al. |
| 2003/0153949 | A1* | 8/2003 | Lau et al. ..................... 606/237 |
| 2003/0171739 | A1 | 9/2003 | Murphy et al. |
| 2005/0245891 | A1 | 11/2005 | McCormick et al. |

OTHER PUBLICATIONS

Rudolph Matas "Ligation of the Abdominal Aorta," Ann. Surg. (1925) 457-464.

Rudolph Matas "Aneurysm of the Abdominal Aorta at its Bifurcation into the Common Iliac Arteries," Annals of Surgery (1940) 112(5):909-922.

Najafi et al. "Rupture on an Otherwise Normal Aortic Valve," Journal of Thoracic and Cardiovascular Surgery (1968) 56(1):57-62.

Graham et al. "Ruptured Abdominal Aortic Aneurysm," Arch Surg. (1968) 97(6):1024-1031.

Parodi et al. "Transfemoral Intraluminal Graft Implantation for Abdominal Aortic Aneurysms," Annals of Vascular Surgery (1991) 5(6):491-499.

Schramel et al. "Studies of Pulmonary Diffusion after Open Heart Surgery," K. Thorac Cardiovascular Surg. (1959) 38:281-91.

Creech et al. "The Surgical Treatment of Acquired Heart Disease Utilizing Extracorporeal Circulation," J. LaState Med. Soc. (1959) 111:319-320.

Blakesmore et al. "Aneurysm of the Aorta: A Review of 365 Cases," Circulation (1954) 5:209.

Dubost et al. "Resection of an Aneursym of the Abdominal Aorta," Arch. Surg. (1952) 64:405-408.

* cited by examiner

EXPANDABLE VESSEL HARNESS FOR TREATING VESSEL ANEURYSMS

CROSS-REFERENCE TO RELATED APPLICATIONS

Pursuant to 35 U.S.C. §119 (e), this application claims priority to the filing date of U.S. Provisional Patent Application Ser. No. 60/639,481 filed Dec. 28, 2004; the disclosure of which application is herein incorporated by reference.

INTRODUCTION

1. Field of the Invention

The present invention relates to mechanical systems for treating vessel aneurysms. Specifically, the invention relates to devices that interface mechanically with a patient's enlarging vessel in order to restrict its continued expansion.

2. Background of the Invention

Aneurysms are defined as a focal dilatation with at least a 50% increase over normal arterial diameter.

One significant clinical problem in which aneurysm formation presents is the phenomenon of abdominal aortic aneurysms (AAAs). AAAs represent a degenerative process of the vessel that is often attributed to atherosclerosis; however, the exact cause is not known. Vesalius described the first AAA in the 16th century. A familial clustering of AAAs has been noted in 15-25% of patients undergoing repair of the problem. Degenerative aneurysms account for more than 90% of all infrarenal AAAs. Other causes include infection, cystic medial necrosis, arteritis, trauma, inherited connective-tissue disorders, and anastomotic disruption. The disease generally affects elderly white men. Smoking appears to be the risk factor most strongly associated with AAA.

Most cases of AAA begin below the renal arteries and end above the iliac arteries. They generally are spindle shaped; however, considerable variation in size, shape, and extent exists. Of AAA cases, 10-20% have focal outpouchings or blebs that are thought to contribute to the potential for rupture. The wall of the aneurysm becomes laminated with thrombus as the blebs enlarge. This can give the appearance of a relatively normal intraluminal diameter in spite of a large extraluminal size.

In general, AAAs gradually enlarge (0.2-0.8 mm/y) and eventually rupture. Hemodynamics play an important role. Areas of high stress have been found in AAAs and appear to correlate with the site of rupture.

Surgical specimens of AAAs reveal inflammation, thinning of the media, and marked loss of elastin. AAAs also demonstrate a chronic adventitial and medial inflammatory infiltrate.

Before the development of a surgical intervention for the process, attempts at medical management failed. In 1923, Matas performed the first successful vessel ligation on a patient. Attempts were made to induce thrombosis by inserting intraluminal wires. In 1948, Rea wrapped reactive cellophane around the aneurysm in order to induce fibrosis and limit expansion. In 1951, Dubost performed the first AAA repair using a homograft.

Prior to this date, vessel aneurysms were treated using a variety of methods, including ligation, intraluminal wiring, and cellophane wrapping. Unfortunately, early homografts became aneurysmal because of preservation techniques. In 1953, Blakemore and Voorhees repaired a ruptured AAA using a Vinyon-N graft (ie, nylon). Later, these grafts were replaced by Dacron and Gore-Tex (ie, polytetrafluoroethylene [PTFE]) fabrics. The final advance was abandonment of silk sutures, which degenerated, in favor of braided Dacron, polyethylene, and PTFE (ie, Gore-Tex) sutures, all of which retain tensile strength.

Postoperative surgical mortality rates initially remained high (>25%) because the aneurysm sac generally was excised. Nearly simultaneously in 1962, Javid and Creech reported the technique of endoaneurysmorrhaphy. This advancement reduced mortality dramatically. Today, operative mortality rates range from 1.8-5%.

In the late 1980s, Parodi described endovascular repair using a large Palmaz stent and unilateral aortofemoral and femorofemoral crossover Dacron grafts. Nowadays, endovascular stent grafting is a procedure where a stent graft, which is a woven polyester tube covered by a tubular metal web, is placed inside of the aneurysm in order to exclude the aneurysm from the circulation.

Patients who have very large aneurysms or who possess angled vessel anatomy may not be able to undergo the procedure, and since the aneurysm is not actually replaced, a risk of aneurysm rupture remains, about 1.5% at four years compared to less than 1% for surgical repair.

Accordingly, a need still exists in the art for a prosthetic device for treatment of vessel aneurysms that eliminates the risks of surgery, specifically secondary to the need for wide intra excision, intestinal manipulation, and intraoperative clamping of the vessel with resultant cardiac stress. This device would also need to resolve issues found with endovascular stent grafting, specifically with regards to a candidate pool limited by aneurysm size and vascular anatomy and the issue of supplemental reinforcement of the aneurysm wall without apparent resolution of hemodynamic considerations.

Abdominal aortic aneurysms are the most appreciated examples of the potential derangement caused by aneurysms. However, aneurysms can present in any vessel with significant intraluminal pressure or wall compromise. Rupture can lead to potentially catastrophic leakage and hemorrhage. Dilatation can induce changes in flow that lead to local effects such as thrombus formation and inflammation, upstream effects such as increased cardiac workload and fatigue requiring autonomic compensation, and downstream effects such as decreased perfusion and nutrition leading to increased risk of necrosis and infection.

SUMMARY OF THE INVENTION

Accordingly, it is a principal object and advantage of the present invention to overcome some or all of the aforementioned disadvantages of existing techniques. One aspect of the present invention comprises a vessel harness for treating or preventing vessel aneurysms, predominantly but not exclusively arteries and arterioles, with relatively high intraluminal pressure capable of exerting transmural distention. The harness comprises a plurality of interconnected elastic bending hinges, each of which has a central portion connected on opposite sides to respective arm portions. The arm portions interact with the central portion in response to deflection of the arm portions to create a bending moment in the hinge to store potential energy.

In certain embodiments, the vessel harness comprises bending hinges that are substantially U-shaped, V-shaped, square-wave-shaped, teardrop-shaped, or keyhole-shaped. Advantageously, at least one of the bending hinges from a first row is connected to another of the bending hinges from a second row.

In some preferred embodiments, the bending hinges comprise at least one strand of Nitinol. The strand(s) can comprise a wire or a ribbon.

In some embodiments, the vessel harness further comprises a power source that supplies energy to the harness, causing the harness to contract. That power source may deliver electrical energy to at least one of the bending hinges, causing at least one of the bending hinges to produce a bending moment. Alternatively, the power source may deliver mechanical energy to the vessel harness, such as through a cable. Advantageously, the power source is programmable via transcutaneous radiofrequency signals, and can be rechargeable via transcutaneous electromagnetic coupling, and/or transcutaneous inductive field coupling.

In another aspect of the invention, the vessel harness has a plurality of spring elements, and the harness is adapted to be placed around the cylindrical form of a vessel. The spring elements interact such that the harness expands and contracts in a substantially transverse dimension of the harness in the region of application in response to hemodynamic forces, without substantial expansion or contraction in the longitudinal dimension of the harness in the region of application.

Another aspect of the invention includes at least one elongate strip sized to fit around the circumference of a vessel, such that the strip extends substantially transverse to the longitudinal axis of the vessel. The strip comprises at least one spring element configured to cause the strip to provide force against the wall of the vessel in a substantially transverse direction without substantial force in a longitudinal direction. The strip can comprise at least one undulating strand.

In some embodiments, the spring element comprises a central portion and two arm portions.

In another aspect, the harness of the disclosed embodiments can treat or prevent vessel aneurysms in a vessel that progressively expands in response to transmitted systolic forces and turbulent local flow. The harness comprises a plurality of interconnected spring elements, limiting systolic distention of the vessel to a degree of expansion without substantially altering naturally occurring changes in the shape of the vessel through the same degree of expansion caused by systolic distention of the vessel. Alternatively, the harness can limit systolic distention of the vessel to a degree of expansion while substantially decreasing the magnitude of a naturally occurring increase in the shape of the vessel through the same degree of expansion caused by systolic distention.

In another aspect of the invention, the harness comprises a series of interconnected spring elements, each spring element comprising a central portion and a pair of arm portions extending along respective paths that originate at respective sides of the central portion and converge toward each other along at least a portion of the paths as the paths extend away from the central portion.

In a further aspect, the harness comprises first and second strands of material, each strand having a plurality of hinges. Each of the hinges is formed by a pair of arm portions extending from a central portion, and each hinge within the plurality of hinges of the first strand has both arm portions disposed within a hinge of the second strand, between the arm portions of the hinge of the second strand. In some embodiments, at least one of the strands comprises a band.

Also disclosed is a method of assembling a vessel harness, comprising providing a plurality of rings, each of the rings having a series of periodic undulations, each of the rings being unattached to other of the rings, and interconnecting the rings by interleaving the undulations without interrupting continuity of the rings.

In certain embodiments, the vessel harness comprises interconnected strands of material. In further embodiments, the harness comprises interconnected strands of material that traverse an exterior surface of the vessel without traversing a substantial portion of the length of any adjunct arteries on its surface.

Hinges can be disposed in helical elements, also referred to in this discussion as rings, rows, or strips around the circumference of the vessel. Strips can contain one or more connected hinges. Hinges in a strip are oriented to have the same axis of elasticity as other hinges in a strip. Strips can be joined or they can be independent of one another. Strips of hinges can be joined by interconnecting elements in a variety of ways.

Joined strips can be linked by longitudinally oriented hinges which act as interconnections between strips. These longitudinally oriented hinges provide elastic recoil in the longitudinal direction, while the strips of hinges provide the usual elasticity in the transverse direction. This arrangement imparts an isotropic elastic structure.

An advantageous feature of the preferred embodiment is the decoupling of the action of the harness in the circumferential or transverse dimension from the longitudinal direction. This decoupling is accomplished by allowing a hinge to stretch or bend circumferentially, or transversely, without pulling much longitudinally on the adjacent hinges.

An additional way that the longitudinal expansion of the harness can be decoupled from the transverse expansion of the harness is through the use of elastically recoiling interconnecting elements. Having interconnecting hinges is an additional way of decoupling longitudinal contraction and expansion of the harness from transverse expansion and contraction of the hinges within the harness.

Another embodiment can be comprised of a variable hinge network, where hinges within a strip vary in height.

Also disclosed is an apparatus for delivering a vessel harness (FIG. 1). The apparatus comprises twin catheter bodies having distal end portions configured to retain the harness in a substantially furled condition, with an interior side of the harness facing towards the vessel and an exterior side facing away from the vessel. A portion of the distal end portions to which harness is attached can be extended while having the remainder of the distal end portion in place so as to extend the length of the harness across the longitudinal breadth of the affected segment of the vessel, effectively spanning the affected segment.

Another aspect of the invention includes a method of delivering a vessel harness onto a vessel (FIG. 2). The method comprises provides twin catheters with the vessel harness mounted on the distal end portions of the catheters, inserting the catheters via a caudad approach oriented in the sagittal plane of the vessel such that the distal end portions of the catheters lie positioned proximate to the vessel oriented roughly along its longitudinal axis (FIG. 2A), extending a portion of the distal end portions to which harness is attached while having the remainder of the distal end portion remain in place such that the affected segment is spanned by harness, and then rotating one of the catheters around the circumference of the vessel (FIG. 2B) so as to span the surface of the affected segment (FIG. 2C).

Also disclosed is as method of manufacturing a vessel harness. The method comprises forming an elongate member having undulations from a sheet of material. In a preferred arrangement, forming the elongate member comprises forming the undulations in a plane substantially parallel to the sheet of material. In some embodiments, forming the elongate member comprises cutting the elongate member on a flat surface, and in certain arrangements, the method further comprises annealing the material with the undulations oriented at a substantial angle relative to the plane.

Further features and advantages of the present invention will become apparent to one of skill in the art in view of the Detailed Description of the Preferred Embodiments that follows, when considered together with the attached drawings and claims.

Before the present invention is further described, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
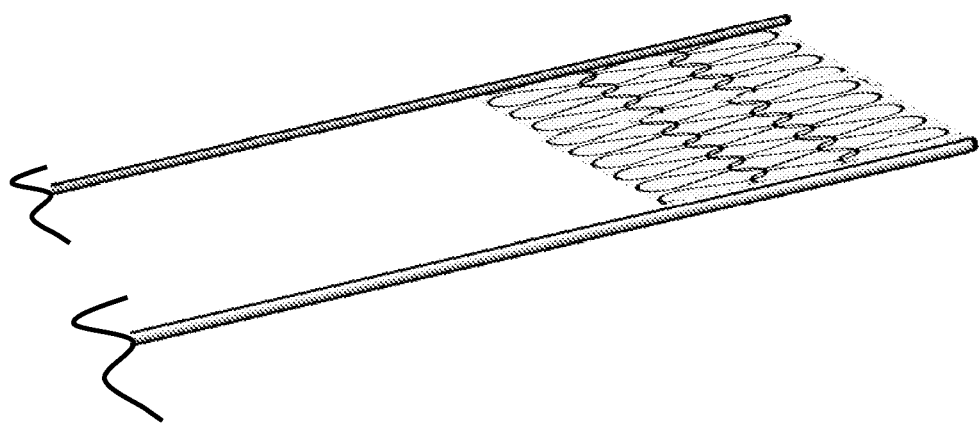
FIG. 1 illustrates an embodiment of a vessel harness provided herein, the vessel harness having twin catheter bodies that include distal end portions configured to retain the harness in a substantially furled condition.
Figure 2:
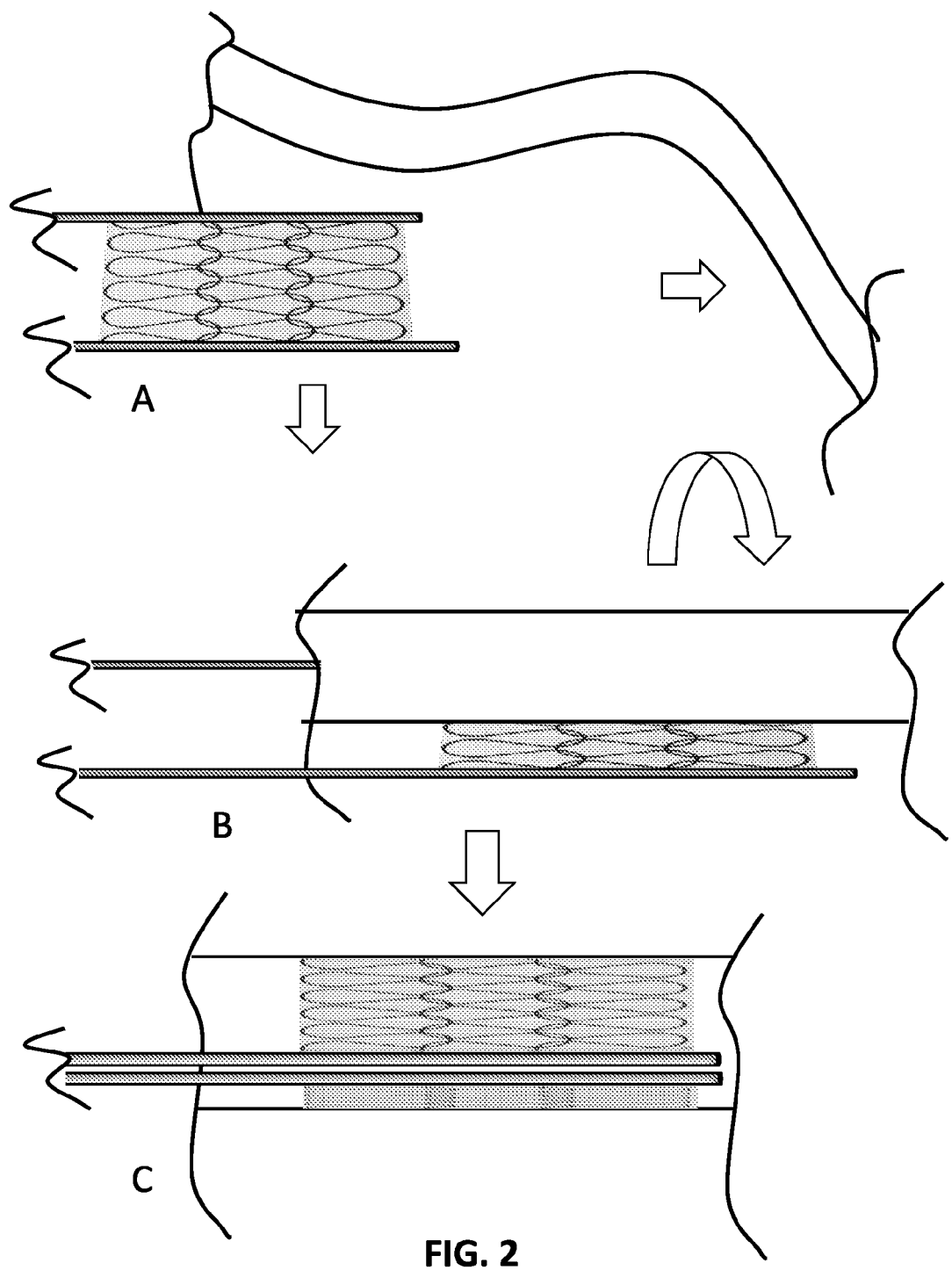
FIG. 2 illustrates a method of delivering a vessel harness onto a vessel (FIG. 2) using twin catheters wherein the harness is mounted to the distal end portions of the catheters. The catheters are inserted via a caudad approach oriented in the sagittal plane of the vessel such that the distal end portions of the catheters lie positioned proximate to the vessel oriented roughly along its longitudinal axis (FIG. 2A), extending a portion of the distal end portions to which harness is attached while having the remainder of the distal end portion remain in place such that the affected segment is spanned by harness, and then rotating one of the catheters around the circumference of the vessel (FIG. 2B) so as to span the surface of the affected segment (FIG. 2C).

An embodiment of the invention comprises an apparatus and method for treating vessel aneurysm, as well as for preventing its onset in patients at risk. Although reference is frequently made throughout this discussion to vessel aneurysm caused by progressive enlargement due to disease of unclear etiology, the vessel harness can be used to treat vessel aneurysm from any disease. The harness acts by the application of a elastic compressive reinforcement on the vessel to reduce deleterious and excessive wall tension and to resist shape change of the vessel during systole. Use of this harness can attenuate and potentially reverse the remodeling process that occurs in the wall of the vessel.

The harness applies compressive reinforcement around the vessel over a significant portion of the cardiac cycle while minimize change to the shape of the vessel. Rather than imposing a dimension beyond which the vessel cannot expand, the preferred embodiment attempts to set no distinct limit to end-diastolic volume. Instead, the apparatus of the preferred embodiment follows the contour of the vessel wall and continuously applies a gentle resistance to wall stretch. This feature avoids the potential to create dangerous restrictive and constrictive conditions that could create turbulent disruptions in local blood flow, leading to thrombus formation and accompanying sequelae.

A great advantage of the harness of the disclosed embodiments is its elasticity. Elasticity refers to the ability of a material or object to deform and recover its shape when a load is first applied and then removed from it. The greater the deformation from which it can recover, the greater is the elasticity of the material or object. Elasticity allows the vessel harness to conform and apply pressure on the vessel as relative flow increases and decreases. Elasticity of the harness is achieved by the use of hinges, which can be U-shaped, that bend elastically under load. These hinges can be arrayed or networked in various ways to impart a desired amount of support in a desired orientation, at a desired location. Another advantageous aspect of the vessel harness is that the hinges are arranged so as to minimize or avoid foreshortening, especially in the longitudinal direction during circumferential expansion. This allows the device to reinforce the vessel without necessarily altering the vessel's shape to a great degree.

In addition to providing passive elastic support of the vessel, the device can also provide an interface to the vessel that allows the application of power to assist hemodynamic function.

A goal of vessel harnessing according to the preferred embodiment is to apply a gentle compressive pressure against the surface of the adventitia of the vessel. As the vessel wall distends locally or globally, it will be met with increasing pressure by the hinges, locally or globally. Increased pressure exerted by the harness lowers wall stress within the vessel and thus may prevent further expansion, global dilatation, and remodeling. The vessel harness according to the preferred embodiment mechanically resists size and shape changes that take place in the vessel as the aneurysm progresses. In addition, the harness may be capable of reversing the remodeling process that occurs with development and progression of the aneurysm. Changes that may occur include decreased local atherosclerosis, decreased metalloproteinase activity, decreased local immune activity, and improvement of endothelial cell function. If reverse remodeling occurs, and the vessel shape and size consequently decrease back toward normal, that resistive pressure from the harness will commensurately decrease, as well.

The application of a vessel harness according to the preferred embodiment during progression of an aneurysm can provide further benefit. By reducing the capacitance created by formation of an aneurysm and maintaining the appropriate dynamic range between systole and diastole, cardiac function may improve. Improvements in laminar short term gains in local blood flow upstream of the harness placement site may occur as well due to the increased resistance created by the action of the harness on the vessel downstream from the ostia of other vessels. Autonomic function may normalize due to restoration of native vessel physiology, which in turn may have further effects on reducing overall systemic inflammation.

Another embodiment comprises a variable hinge network. This variable hinge network provides the capability to tailor the stiffness of the harness such that the stiffness varies with the degree of stretch. This arrangement can advantageously provide a pressure versus diameter curve for the harness that exhibits two distinct stiffness peaks at different diameters—with diameter corresponding to ventricular wall stretch or degree of distension.

An important difference between the decoupled hinge harness construction of the preferred embodiment and a knitted fabric endovascular graft is the preservation of the native intimal lining of the vessel with the former approach. Endothelial cell function is consequently preserved and likely will lead to promotion of local repair and reverse remodeling. Thrombosis is likewise discouraged by the absence of visible potentially immunogenic foreign elements contacting or replacing the intima either during or subsequent to placement. Disruption or injury to the intima is known to promote both inflammation and thrombogenesis.

A preferred embodiment comprises an array of connected hinge elements that are configured to be in compressive contact with the vessel. The array of hinge elements provides selective elastic resistance to stretch during systole and contractile augmentation during diastole. Typically, elastic materials resist deformation with a force that increases with increasing deformation. This force is stored in the material and is released during the unloading of the material. Because wall stress in the vessel is thought to be greater in the circumferential direction, the hinges are predominantly aligned to act in this direction, although it may be desirable to have some elastic support in the longitudinal direction, or some other direction, as well.

Hinges can be disposed in helical elements, also referred to in this discussion as rings, rows, or strips around the circumference of the vessel. Strips can contain one or more connected hinges. Hinges in a strip are oriented to have the same axis of elasticity as other hinges in a strip. Strips can be joined or they can be independent of one another. Strips of hinges can be joined by interconnecting elements in a variety of ways.

Joined strips can be linked by longitudinally oriented hinges which act as interconnections between strips. These longitudinally oriented hinges provide elastic recoil in the longitudinal direction, while the strips of hinges provide the usual elasticity in the transverse direction. This arrangement imparts an isotropic elastic structure.

An advantageous feature of the preferred embodiment is the decoupling of the action of the harness in the circumferential or transverse dimension from the longitudinal direction. This decoupling is accomplished by allowing a hinge to stretch or bend circumferentially, or transversely, without pulling much longitudinally on the adjacent hinges.

An additional way that the longitudinal expansion of the harness can be decoupled from the transverse expansion of the harness is through the use of elastically recoiling interconnecting elements. Having interconnecting hinges is an additional way of decoupling longitudinal contraction and expansion of the harness from transverse expansion and contraction of the hinges within the harness.

Another embodiment can be comprised of a variable hinge network, where hinges within a strip vary in height. This variable hinge network provides the capability to tailor the stiffness of the harness such that the stiffness varies with the degree of stretch. This arrangement can advantageously provide a pressure-versus-diameter curve for the harness that exhibits different stiffness peaks at different diameters—with diameter corresponding to wall stretch or degree of distension.

Another important difference between the decoupled hinge harness construction of the preferred embodiment and a knitted fabric endovascular graft is the hinge harness's ability to closely track changes in shape of the underlying vessel, whether the vessel is healthy or diseased. Studies with inflated latex bladders have demonstrated that sphericity-versus-volume curve application of the elastic hinge harness more closely matched that of the unencumbered bladder alone.

The hinges can be made of a variety of materials, including metals, polymers, composites, ceramics, and biologic tissue. Specific materials include stainless steel, Elgiloy, titanium, tantalum, Nitinol, ePTFE, collagen, nylon, polyester, and urethane. Advantageously, the hinges are made from a metal, particularly Nitinol, because metals have a higher Young's modulus or stiffness, than polymers or tissue. This allows less mass and volume of material to be used to achieve the same mechanical reinforcing strength. Prosthetic materials directly applied to organic substrates can potentially induce inflammation or fibrosis; consequently, an implant with less surface tends to have lower risk of this development.

Nitinol is especially suitable for the construction of the harness. It has the advantageous capability of being able to remain elastic over a great range of strain, up to 4%, which is greater than other materials. It generates a relatively benign foreign body response from tissue, and it is relatively magnetic-resonance-imaging-compatible, as it is not highly ferromagnetic. Nitinol is also corrosion- and fatigue-resistant. In addition, metal such as Nitinol are more creep-resistant than polymeric or tissue-based materials.

The hinge elements can be made from wire, or they may be machined from sheet or tubing material, or a combination thereof.

In addition to varying the direction of elastic support, the extent of support or stiffness can be varied. Hinges of different shape or of different material dimensions can accomplish this. Instances where differential stiffness of the harness is desired can be realized in several ways. Hinges apposed to the surface for which increased stiffness is desired can be made thicker, small, or with stiffer material. A wire or plastic frame comprising two struts can be integrated with the harness. Such a frame would exert a claming pressure along vectors 180 degrees apart, limiting the amount the intervening surface is allowed to distend. The amount of pressure exerted by the frame can be adjusted by making the frame larger or smaller, or thicker or thinner. The harness can also feature more than one frame. The harness's hinges positioned between the frames, or between struts of frames, can be of varying thickness, size, or material to apply varying stiffness as well.

In another embodiment, the vessel harness may be selected applied to only one aspect of the vessel, depending on which aspect of the vessel is most diseased. Anchoring of the harness to the vessels can occur in a variety of ways, including having anchoring struts extending into the vessel wall. Coverage of the affected area of the vessel ensures maximum reinforcement both globally, to attenuate global shape change and dilatation, and locally, to prevent wall thinning and stretch in a particular area.

The compliance of the elastic harness is in the range of compliance of the native vessel wall. The compliance of the harness increases gradually as a function of stretch. Over the operational range of the harness, compliance should not fall so low that the harness becomes constrictive.

Various designs incorporating decoupled hinges are possible. The hinges can wrap continuously around the vessels or a single aspect of the vessel. The harness can have a seam for size adjustment, or it can be of a one-size-fits-all design. It can be provided presized to fit the dimensions of the vessel in question. Alternatively, the harness components can be provided in a kit that a surgeon can custom-assemble in the operating room based on sizing information gained before or at the time of surgery.

Delivery of the harness can be accomplished through conventional surgical techniques through a trans-abdominal approach. Alternatively, the harness may be delivered through minimally invasive surgical access to the surrounding space. Preferably, such a minimally invasive procedure is accomplished without the use of vessel clamping or other compromise of native blood flow. The delivery system of the disclosed embodiments compromises an integrated unit of several components. Preferably, there is a releasable suction device such as a suction cap on the lateral aspect of the proximal component of the distal tip of the delivery device. This negative pressure suction cup is used to hold the delivery device in close approximation to the vessel caudad to the aneurysm. Negative pressure can be applied to the cup using a syringe or other vacuum device. A negative pressure lock can be achieved through a one-way valve, stopcock, or a tubing clamp. The suction cup, advantageously formed of a biocompatible material, is preferably stiff to prevent any negative pressure loss through vessel manipulation. This provides traction by which the second component of the distal tip can be extended with harness trailing and then rotated around the circumference of the vessel. In addition, the suction cup can be used to reposition the vessel to facilitate placement of the harness or to allow visualization and manipulation of the posterior side of the vessel.

After secure purchase of the vessel caudad to the aneurysm, the harness, which is collapsed within the body of the delivery device, is advanced in a rolled form cephalad along the length of the vessel by a combination of extension of the distal component of the distal tip of the delivery device and actuating fingers, until it spans the length of the affected segment of the vessel containing the aneurysm. A second suction cup can then be deployed. This second negative pressure cup is used to hold this portion of the delivery device such that it effectively extends the harness to span the affected segment. The harness can then be unrolled by rotating the delivery device around the circumference of the vessel. Excess harness would remain packaged. After the harness is advanced into place, the suction is released and the delivery system is released from the harness and vessel.

The harness can be secured in place on the vessel using sutures or staples to prevent it from migrating. Alternatively, the harness can self-anchor to the vessel to prevent it from migrating. This self-anchoring can be accomplished incorporating inward-facing barbs or anchors in the harness structure. The anchors preferably extend from the hinges into the wall of the vessel.

The harness not only has the capability of acting as a passive restraint around the heart, but may also be actively powered to provide contractile assistance during systole. This may be done by the application of electrical or mechanical power to the harness.

If electrical current or heat is applied to the harness in the stressed state, the resistive force generated by the bending deformation increases. In essence, the harness generates a contractile force when current is applied to the harness. Hence, it is possible actively power an otherwise passive elastic harness in order to achieve hemodynamic assistance. This effect is additional to any vessel wall sparing benefit that the harness provides.

Current can be applied to the harness to make it contract and thus assist in vessel flow. One such mechanism involves surrounding the vessel in question with the harness and having an electrical wire extend from an internal power supply to the harness.

The internal power supply is a device that supplies electrical energy to the harness. It may also comprise a battery and, in some embodiments, a radiofrequency transducer for receiving and/or transmitting radiofrequency signals to and from an external radiofrequency transducer which may send and/or receive signals from the internal power supply. The external RF transducer may recharge a battery within the internal power supply. The external RF may also be used to send program information from the external RF transducer to the internal power supply or vice versa regarding electromechanical sensing and/or pacing information, cardiac rhythm, degree of vessel or harness contractility, heart rate information, or similar data. Alternatively the external RF transducer may supply electrical power through inductive field coupling between the external RF transducer and the internal power supply.

In some embodiments, an external power supply can be used, which may be a battery pack in various preferred arrangements. The external power supply may supply current to the external RF transducer, which may in turn supply electrical energy to the internal power supply through inductive field coupling. The technology for this inductive field coupling, including electronic programming and power transmission through RF inductive coupling, has been developed and is in employed in various cardiac and neurologic stimulation and assistance devices.

The power requirement of the device of the disclosed embodiments is significantly lower than might be expected because the powered merely augments any native hemodynamic processes already in play.

Rather than a Nitinol harness providing active assistance, variable current can be applied directly to the Nitinol to simply vary the harness's passive stiffness. As such, power is not used to actively "squeeze" the heart during systole. The harness is instead a passive elastic harness with adjustable compliance. The power to a harness can be adjusted to vary the amount of resistive pressure exerted on the vessel during both systole and diastole. The passive stiffness of the harness can be set to change throughout the cardiac cycle, or it can be adjusted to maintain constant levels. Adjustment and stimulation of the harness can be accomplished through an implantable pacemaker-like box, the internal power supply, electrically connected to the harness through at least one wire. The harness may be integrated with other electrical devices, such as a pacemaker or defibrillator, according to patient needs.

Mechanical power can be applied to the harness through sliding cables. A cable can extend over the surface of the harness between two points. The cable is actually an inner sliding element that resides partially with an outer housing. Mechanical actuation of the cable causes the two components to slide or otherwise move relative to each other. If the end of the housing is attached to a strut, and the distal end of the cable is attached to another strut, then actuation of the cable can cause the two struts to move closer and/or farther apart relative to one another, causing the heart to contract and/or expand, thereby providing another mechanism by which contractile assistance can be provided.

Although the present invention has been described in terms of certain preferred embodiments, other embodiments that are apparent to those of ordinary skill in the art are also within the scope of the invention. Accordingly, the scope of the invention is intended to be defined only by reference to the appended claims.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a vessel aneurysm, the method comprising:
    placing a vessel harness comprising a plurality of interconnected elastic bending hinges circumferentially around a vessel aneurysm such that the aneurysm is spanned by the harness, wherein the harness is configured to apply a compressive pressure against a surface of the adventitia of the vessel, wherein the harness is placed using a minimally invasive approach;
    providing twin catheters with the vessel harness mounted on distal end portions of the catheters;
    inserting the catheters such that the distal end portions of the catheters lie positioned proximate to the vessel oriented along its longitudinal axis;
    extending a portion of the distal end portions to which the harness is mounted while a remainder of the distal end portions of the catheters remain in place, such that a longitudinal extent of the aneurysm of the vessel is spanned by the harness; and
    rotating one of the catheters around the circumference of the vessel so as to span a surface the aneurysm.

2. The method according to claim 1, wherein the vessel aneurysm is an aortic aneurysm.

3. A method of preventing a vessel aneurysm, the method comprising:
    providing a subject at risk for developing a vessel aneurysm; and
    placing a vessel harness comprising a plurality of interconnected elastic bending hinges circumferentially around a vessel at risk for developing an aneurysm, wherein the harness is configured to apply a compressive pressure against a surface of the adventitia of the vessel, wherein the harness is placed using a minimally invasive approach;
    providing twin catheters with the vessel harness mounted on distal end portions of the catheters;
    inserting the catheters such that the distal end portions of the catheters lie positioned proximate to the vessel oriented along its longitudinal axis;
    extending a portion of the distal end portions to which the harness is mounted while a remainder of the distal end portions of the catheters remain in place, such that a longitudinal extent of a segment of the vessel at risk is spanned by the harness; and
    rotating one of the catheters around the circumference of the vessel so as to span a surface of the segment of the vessel at risk.

4. The method according to claim 3, wherein the harness is configured to apply a compressive pressure over a significant portion of a cardiac cycle of the subject, such that the increased pressure exerted by the harness lowers wall stress within the vessel and thereby prevents further expansion of the vessel.

5. The method according to claim 3, wherein the vessel is the aorta.

* * * * *